(12) United States Patent
Chew

(10) Patent No.: US 12,383,904 B2
(45) Date of Patent: Aug. 12, 2025

(54) DEVICE FOR MANIPULATING SAMPLES

(71) Applicant: STEMCELL TECHNOLOGIES CANADA INC., Vancouver (CA)

(72) Inventor: Leon Chew, Vancouver (CA)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 0 days.

(21) Appl. No.: 18/588,665

(22) Filed: Feb. 27, 2024

(65) Prior Publication Data
US 2024/0207855 A1    Jun. 27, 2024

Related U.S. Application Data

(63) Continuation of application No. 16/527,177, filed on Jul. 31, 2019, now abandoned.

(60) Provisional application No. 62/713,189, filed on Aug. 1, 2018.

(51) Int. Cl.
*B01L 3/00* (2006.01)
*C12M 1/32* (2006.01)

(52) U.S. Cl.
CPC .......... *B01L 3/5085* (2013.01); *C12M 23/12* (2013.01); *B01L 2300/0829* (2013.01)

(58) Field of Classification Search
CPC .............. B01L 3/5085; B01L 3/5088; B01L 2300/0819; B01L 2300/0829; B01L 2300/0893; B01L 2300/123; C12M 23/12; C12M 25/04
See application file for complete search history.

(56) References Cited

U.S. PATENT DOCUMENTS

| | | | |
|---|---|---|---|
| 3,787,290 A | 1/1974 | Kaye | |
| 4,956,150 A | 9/1990 | Henry | |
| 5,969,814 A * | 10/1999 | Barber | G01N 21/532 356/338 |
| 2009/0298116 A1 | 12/2009 | Fang et al. | |
| 2012/0244567 A1* | 9/2012 | Zeng | G01N 33/5073 435/405 |
| 2014/0051788 A1 | 2/2014 | Suzuki | |
| 2016/0053293 A1 | 2/2016 | Broder et al. | |
| 2018/0201891 A1 | 7/2018 | Ubukata et al. | |

FOREIGN PATENT DOCUMENTS

WO    WO-9858254 A1 *  12/1998  ............. G01N 33/15

* cited by examiner

*Primary Examiner* — Jill A Warden
*Assistant Examiner* — Dwayne K Handy
(74) *Attorney, Agent, or Firm* — SMART & BIGGAR LP; Micheline Gravelle

(57) ABSTRACT

This disclosure is directed to a method and device for manipulating a sample, such as a biological sample. A device of this disclosure includes mat having a top planar surface spaced apart from a bottom planar surface and a recess formed in the top planar surface extending toward the bottom planar surface, the recess having an opening at the top planar surface and bounded by a non-planar bottom wall. By way of example, a device of this disclosure may be used to embed an aggregate of cells, such as an embryoid body or a neuralized embryoid body, within extracellular matrix.

17 Claims, 3 Drawing Sheets

DEVICE FOR MANIPULATING SAMPLES

CROSS REFERENCE TO RELATED APPLICATION

This application is a continuation of U.S. patent application Ser. No. 16/527,177 filed Jul. 31, 2019, which claims the benefit of U.S. Provisional Application No. 62/713,189 filed Aug. 1, 2018, the entire contents of both are incorporated herein by reference.

FIELD

This disclosure relates to methods and devices for carrying out small-scale mixing and/or suspending or embedding operations. More particularly, this disclosure relates to methods and devices for carrying out routine laboratory protocols or assays, such as manipulating samples in protocols or assays.

BACKGROUND

In various processes it is desirable to mix relatively small volumes of liquids or to suspend or embed substances within a relatively small volume of liquid(s). Such mixing or embedding is commonly done in manufacturing, quality testing, or laboratory experimentation in the physical or life sciences. In particular instances, such mixing or embedding is an intermediate step in a process, and the product of mixing or embedding is used in downstream protocols or assays.

Mixing and embedding operations may be performed in a vessel or on a planar surface. Examples of vessels may include tubes, such as centrifuge tubes or the like, or plates, such as multi-well plates or the like. Examples of planar surfaces may include a sheet of, for example, plastic or wax film.

However, current approaches to mixing relatively small volumes of liquids or suspending or embedding substances within a relatively small volume of liquid or semi-solid liquid pose certain problems and/or challenges. First, the use of vessels or surfaces for the foregoing purposes may result in the generation of significant amounts of waste. Also, such vessels or surfaces, particularly among frequent users, may require not insignificant storage space. Next, the rigidity of vessels or surfaces may also create problems or challenges related to breakage or shattering. Further, the removal of samples from rigid vessels or surfaces or those having steep wall architectures may be challenging, particularly when the sample is solid, semi-solid, or solidified within the vessel or on the surface. Next, certain vessels or surfaces may also inadequately segregate one prepared mixture from another mixture prepared in the same vessel or on the same surface. When mixtures are not adequately segregated from one another, the risk of contamination is increased. Also, certain vessels or surfaces may not be sterile or readily sterilizable, further contributing to the risks of contaminated mixtures.

Thus, there is a need for devices that enable the more efficient completion of small-scale mixing and embedding operations.

SUMMARY

In a broad aspect of this disclosure is provided a device for manipulating a sample, such as a biological sample. In one embodiment the sample is a biological sample. In one embodiment the biological sample is an aggregate of cells, optionally the aggregate of cells is of human origin. In one embodiment the aggregate of cells is an embryoid body, spheroid, organoid, or an assembloid. In one embodiment the aggregate of cells is a neuralized embryoid body.

In a different broad aspect of this disclosure is provided a device for embedding an aggregate of cells into an extracellular matrix.

In either aspect, the device comprises a mat having a top planar surface spaced apart from a bottom planar surface, and a recess formed in the top planar surface extending toward the bottom planar surface, the recess having an opening at the top planar surface and bounded by a non-planar bottom wall.

In some embodiments, a depth of the recess measured vertically from the center of the opening to the bottom wall is less than a width of the opening.

In some embodiments, the bottom wall is substantially smooth. In the same or different embodiments, the bottom wall is arcuate.

In some embodiments, the device further comprises a plurality of recesses.

In some embodiments, the bottom planar surface is substantially smooth.

In some embodiments, the device may further comprise a second recess formed in the bottom planar surface extending toward the top planar surface, the second recess having a second opening at the bottom planar surface and bounded by a second non-planar bottom wall. In one embodiment, the device further comprises a plurality of second recesses.

In some embodiments, the mat is resilient.

In some embodiments the mat is homogeneous. In the same or different embodiments, the mat is silicone-based. In some embodiments, the mat further comprises an anti-static additive.

In some embodiments, the mat is sterilizable. In some embodiments, the mat is autoclavable.

In some embodiments, the mat is dimensioned to fit within a well of a culture vessel. In some embodiments, more than one mat fits within the well of the culture vessel.

In some embodiments, the device may further comprises an orientation marker.

Other features and advantages of the present disclosure will become apparent from the following drawings and detailed description. It should be understood, however, that the detailed description and the specific examples while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

DETAILED DESCRIPTION

Figure 1:
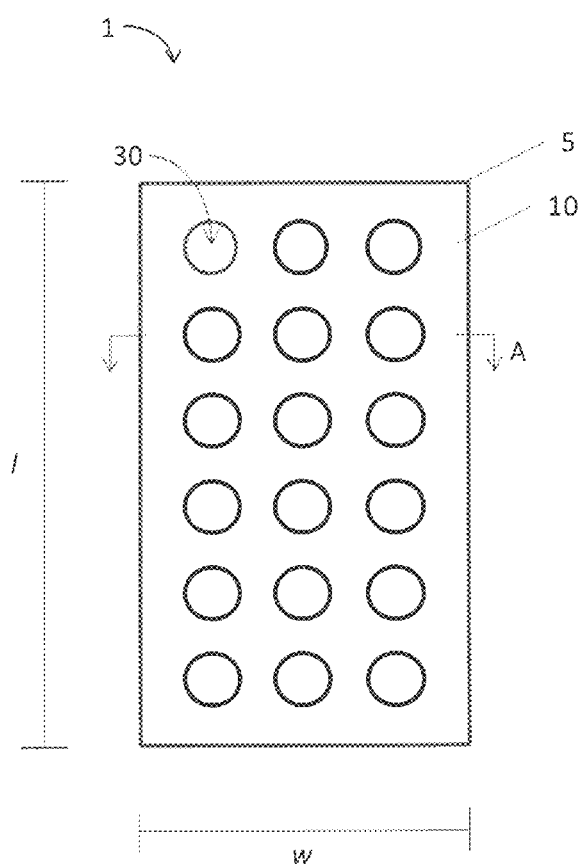
FIG. 1 shows a top plan view of one embodiment of a device for manipulating a sample.

Various devices are described below to provide an example of at least one embodiment of the claimed subject matter. No embodiment described below limits any claimed subject matter and any claimed subject matter may cover devices that differ from those described below. The claimed subject matter is not limited to devices having all of the features of any one device described below or to features common to multiple or all of the devices described below. Subject matter that may be claimed may reside in any combination or sub-combination of the elements disclosed in any part of this document including its claims and figures. Accordingly, it will be appreciated by a person skilled in the art that a device disclosed in accordance with the teachings herein may embody any one or more of the features contained herein and that the features may be used in any particular combination or sub-combination that is physically feasible and realizable for its intended purpose.

Furthermore, it is possible that a device described below is not an embodiment of any claimed subject matter. Any subject matter that is disclosed in a device described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

It will also be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

The disclosure describes a device for manipulating a sample 1. The sample can be a liquid (e.g. a solution, a chemical, etc.), a mixture of liquids, or a combination of a non-liquid substance with a liquid or a mixture of liquids.

In some embodiments the sample comprises a biological sample. More specifically, the biological sample may comprise one or more of nucleic acid(s), protein(s), virus(es), organelle(s), extracellular vesicle(s), exosome(s), cell(s), tissue(s) or tissue fragment(s). In some embodiments the biological sample derives from a prokaryote. In some embodiments the biological sample derives from a eukaryote. In some embodiments the biological sample is mammalian. In some embodiments the biological sample is mouse- or human-derived.

In some embodiments the biological sample comprises nucleic acid and/or protein. In some embodiments the biological sample comprises nucleic acid and/or protein enriched for a specific species (i.e. such as after a PCR or RT-PCR experiment or purification of an over-expressed or labelled protein). In some embodiments the nucleic acid and/or protein is not enriched for a specific species, and may correspond to a bulk preparation from one or more cells or tissues.

In some embodiments the biological sample comprises cells. In some embodiments the biological sample comprises a plurality of cells, wherein the plurality of cells may be enriched for one or more particular cell-types.

In some embodiments, the sample comprises a plurality of cells and the cells may be comprised in a suspension of cells, an aggregate of cells, such as an embryoid body or an aggregate of pluripotent stem cells, or a higher order structure of cells, such as an organoid. In a specific embodiment the biological sample is a tissue fragment, an organoid, a spheroid, or an assembloid.

Figure 2:
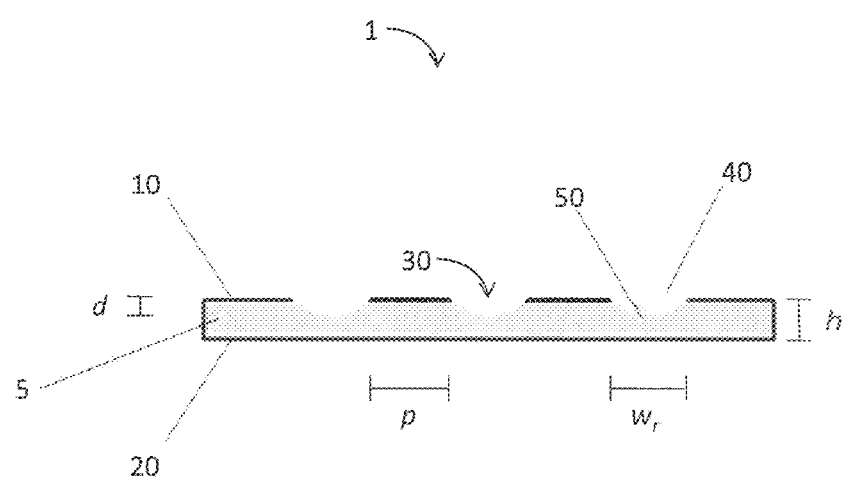
FIG. 2 shows a front view of a device for manipulating a sample taken through line A.

A device of this disclosure 1 comprises a mat 5 having a top planar surface 10 spaced apart from a bottom planar surface 20 (FIG. 1 and FIG. 2). Mat 5 may be formed using any technique capable of creating a desired pattern on a surface of a mat. For example, the mat may be formed by injection molding or 3D printing. In another example, an unpatterned mat may be formed by injection molding or 3D printing, with the patterning subsequently added such as by impression, stamping, or scoring. Or, a large patterned mat may be formed as described above, which may subsequently be cut down into mats having desired dimensions.

Mat 5 may be any polygonal shape or may be modified by a user to a shape that suits the use to which it is put. Thus, mat 5 may be readily manipulatable using scissors, shears, or a knife. In some embodiments mat 5 is a quadrilateral prism.

In embodiments where mat 5 is a quadrilateral prism, mat 5 will have a length l, a width w, and a height h. In such embodiments, mat 5 may assume any dimension, which may correspond to a length/of about 1, 2, 3, 4, 5, 6, 7, 8, 9 or 10 cm, a width w of about 1, 2, 3, 4, 5, 6, 7, 8, 9, or 10 cm, and a height h of about 0.1, 0.2, 0.3, 0.4, 0.5, 0.6, 0.7, 0.8, 0.9, or 1 cm. In a specific embodiment, mat 5 may have a length/of about 5 cm, a width w of about 3 cm, and a height h of about 0.2 cm.

In one embodiment, mat 5 is dimensioned to fit within a well of a culture vessel. The culture vessel may be any standard type of cell culture vessel. For example, the culture vessel may be a petri dish, a 10 $cm^2$ plate, or a multi-well plate, such as a 6-, 12-, or 24-well plate. Thus, mat 5 may be circular and may snuggly fit within the cell culture vessel or a well thereof or mat 5 may be dimensionally smaller than the cell culture vessel or well thereof. In some embodiments, mat 5 is dimensioned so that more than one mat 5 may fit within a well of a culture vessel.

Mat 5 may be made of any material provided it is capable of receiving, containing and supporting a sample thereon. In some embodiments, mat 5 is homogeneous. A homogeneous mat would be formed of a single substance, whether pure or a homogeneous mixture of several components. Thus, in some embodiments mat 5 has a uniform composition.

In some embodiments the material from which mat 5 is formed comprises a polymer. In some embodiments the polymer is silicone-based. In one embodiment, the polymer is a silicone rubber compound. In a more specific embodiment, mat 5 comprises one or more of or consists of dimethylchloro siloxane (polymer), dimethylchloro vinyl, silicone oil, fumed silica, and a catalyst (e.g. a peroxide compound).

In some embodiments the material from which mat 5 is formed may further comprise an anti-static additive. The anti-static additive may be any substance capable of being combined with the material from which mat 5 is made. In some embodiments, the anti-static additive is combined with the material from which mat 5 is made prior to forming mat 5. In some embodiments, the anti-static additive is applied after mat 5 is formed. In some embodiments, the anti-static additive may be added to only one or more surfaces of mat 5, such as top planar surface 10 or bottom planar surface 20 (including bottom walls 50—see below), or both.

In some embodiments mat 5 may be hydrophilic. In some embodiments mat 5 may be hydrophobic. In some embodiments, either a hydrophilic or hydrophobic additive may be combined with the material from which mat 5 is made. In some embodiments, a hydrophilic or hydrophobic coating may be added to only one or more surfaces of mat 5, such as top planar surface 10 or bottom planar surface 20, or both.

In some embodiments mat 5 is resilient. As previously mentioned, mat 5 may be manipulatable which in one respect may mean that its shape may be modified by the user. Mat 5 may also be bendable or foldable but resile to its original shape afterward. A benefit of resilience is that mat 5 may be resistant to shattering or breaking. A further benefit is that mat 5 may be conformable with or redimensioned to the shape of a cell culture vessel or a well thereof.

In some embodiments mat 5 is sterilizable. In one embodiment mat 5 is sterilizable by gamma irradiation, such as at 15 kGy. In the same or a different embodiment, mat 5 is autoclavable, such as at between about 100° C. to 250° C.

Mat 5 comprises a recess 30 formed in top planar surface 10 extending toward bottom planar surface 20 (FIG. 1 and FIG. 2), but not so as to create a bore therethrough. In some embodiments top planar surface 10 comprises a plurality of recesses. In embodiments comprising a plurality of recesses, the plurality of recesses may be arranged in an array of rows and columns. For example, mat 5 may comprise 1, 2, 3, 4, 5, 6, 7, 8, 9, 10, or more rows of recesses along length l thereof, and may comprise 1, 2, 3, 4, 5, 6, 7, 8, 9, 10, or more rows of recesses along width w thereof. In a specific embodiment, but not intended to be in any way limiting, mat 5 comprises 6 rows of recesses by 3 columns of recesses.

In embodiments comprising a plurality of recesses, two adjacent recesses thereof may be separated by a pitch p, as measured from a centerpoint of a first recess and a centrepoint of a second recess. Pitch p may be any distance provided that the contents of two adjacent recesses may still be adequately segregated from one another. In some embodiments, pitch p may be about 0.1, 0.2, 0.3, 0.4, 0.5, 0.6, 0.7, 0.8, 0.9, or 1.0 cm, or more. In a specific embodiment pitch p is between about 0.5 and 1 cm.

It is also possible that an edge of a first recess and an edge of an adjacent second recess are separated from one another by about 1.0, 0.9, 0.8, 0.7, 0.6, 0.5, 0.4, 0.3, 0.2, 0.1, 0.05 cm, or less. In a specific embodiment the edge of the first recess and the edge of the adjacent second recess is between about 0.2 and 0.5 cm.

In some embodiments, only top planar surface 10 comprises a recess 30 (or a plurality of recesses), and in such embodiments bottom planar surface 20 is smooth or substantially smooth (i.e. lacks a recess). In different embodiments, a recess 30 or a plurality of recesses may also be formed in bottom planar surface 20 extending toward top planar surface 10, but not so as to create a bore therethrough.

For clarity, any description of a recess, or a plurality of recesses, in this disclosure which appears to pertain only to those formed in top planar surface 10, may be equally applicable to a recess or a plurality of recesses formed in the bottom planar surface 20, unless a contrary intention is specifically indicated.

As shown in FIG. 2, recess 30 comprises an opening 40 in top planar surface 10. Opening 40 may be coplanar with top planar surface 10 or may be raised from top planar surface 10 if, for example, opening 40 is surrounded by a rim (not shown). Opening 40 may take the form of any shape, but opening 40 is preferably circular, or substantially circular.

As further shown in FIG. 2, recess 30 is bounded by a bottom wall 50. In some embodiments, bottom wall 50 may be flat or substantially flat and in a plane parallel to opening 40. In such embodiments bottom wall 50 is connected to opening 40 by one or more sidewalls (not shown).

In some embodiments, bottom wall 50 may be non-planar. For example, non-planar bottom wall 50 may be curved or arcuate. Where bottom wall 50 is curved or arcuate, bottom wall 50 may be connected to a mouth of opening 40 by one or more sidewalls. Where bottom wall 50 is curved or arcuate it may also be continuous with the one or more sidewalls—in such embodiments the transition between bottom wall 50 and the one or more sidewalls may not be apparent (i.e. there is no distinct transition between bottom wall 50 and the one or more sidewalls).

In the embodiment shown in FIG. 2, a cross-sectional shape of recess 30 taken in a plane orthogonal to the plane of opening 40, bottom wall is curved or arcuate and continuous from a first edge of opening 40 to an opposed edge of opening 40. In some embodiments, a cross-sectional shape of recess 30 taken in a plane orthogonal to the plane of opening 40 is semi-circular, or substantially semi-circular.

In some embodiments, bottom wall 50 is smooth, or substantially smooth. A smooth or substantially smooth bottom wall 50 may help in the recovery of the contents of recess 30, such as by reducing friction. Further, the absence of a sharp edge or corner on the smooth or substantially smooth bottom wall 50 may also help in the recovery of the contents of recess 30. Still further an anti-static or a hydrophilic or a hydrophobic coating may also aid in the recovery of the contents of recess 30.

As shown in FIG. 2, recess 30 has a depth d, wherein depth d is measured vertically from the center of opening 40 at top planar surface 10 to bottom wall 50. Depth d of recess 30 is less than height h of mat 5. For example, depth d may be about 0.05, 0.1, 0.2, 0.3, 0.4, 0.5, 0.6, 0.7, 0.8, or 0.9, or 1 cm. In an embodiment where height h is about 0.2 cm, depth d may be about 0.1 cm.

Also as shown in FIG. 2, recess 30 has a width $w_r$, wherein width $w_r$ is measured across opening 40 along the plane of top planar surface 10. In embodiments where opening 40 is circular or substantially circular, width w, is measured across the diameter of opening 40 along the plane of top planar surface 10. For example, width w, may be about 0.1, 0.2, 0.3, 0.4, 0.5, 0.6, 0.7, 0.8, or 0.9, 1.0, 1.1, 1.2, 1.3, 1.4, 1.5, 1.6, 1.7, 1.8, 1.9, or 2.0 cm, or more. In an embodiment where depth d is about 0.1 cm, width w, may be about 0.5 cm.

In some embodiments, depth d of recess 30, measured vertically from the center of opening 40 at top planar surface 10 to bottom wall 50, is less than width w, of opening 40.

In some embodiments comprising a plurality of recesses 30, each of plurality of recesses 30 may have the same volume. In such embodiments, the dimensions of each of plurality of recesses 30 may be the same. In other embodiments, the volume of each of plurality of recesses 30 may not be the same.

Mat 5 may further comprise an orientation marker 70. Orientation marker 70 may be useful for orienting mat 5 in order to keep track of the contents of recesses 30. In some embodiments, orientation marker 70 may comprise an insignia or a demarcation. On the one hand, examples of an insignia include an image, such as a logo or trademark, or a word element or phrase, such as tradename or trademark. On the other hand, examples of a demarcation may include a structural element, such as a notch cut from or a protrusion from mat 5.

Figure 3:
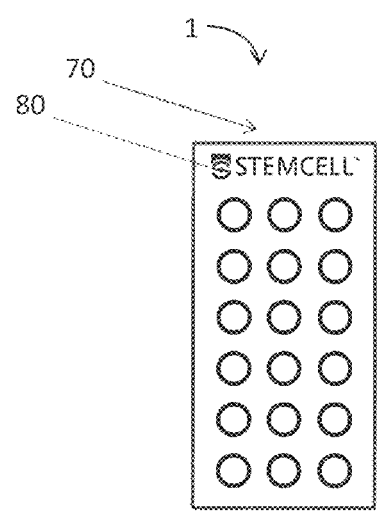
FIG. 3 shows a top plan view of an alternative embodiment of a device for manipulating a sample comprising an orientation marker.

In one embodiment of mat 5 comprising an indicia, a portion of either top planar surface 10 or bottom planar surface 20, or both, may include an area 80 devoid of recesses 30 for displaying such indicia (FIG. 3). Area 80 need only be large enough to accommodate such an indicia. For example, area 80 may extend along length/of mat 5 by about 0.1, 0.2, 0.3, 0.4, 0.5, 0.6, 0.7, 0.8, 0.9 or 1.0 cm, or more. In one embodiment, area 80 extends along length/of mat 5 by about 0.5 cm.

In one specific aspect, device 1 of this disclosure may be used in methods of embedding one or more aggregates of cells in a polymerizable solution, such as a solution comprising extracellular matrix proteins (e.g Matrigel®), within recess 30 of mat 5. In some embodiments the one or more aggregates of cells may be a higher order structure such as an embryoid body, an organoid, a spheroid, an assembloid, or a tissue or a tissue fragment. In some embodiments the one or more aggregates of cells may be stem cells or stem cell-derived. In some embodiments the one or more aggregates of cells may be pluripotent stem cells or pluripotent stem cell-derived.

In a first step, a volume of a polymerizable solution may be dispensed into one or more recesses 30 of mat 5. Before the polymerizable solution becomes polymerized a volume of a solution comprising the one or more aggregates of cells may be pipetted into the volume of polymerizable solution. The combination of polymerizable solution and the volume of solution comprising the one or more aggregates is then allowed to polymerize.

Once the polymerizable solution has polymerized to envelope the aggregate or higher order structure of cells, the enveloped mass may be dislodged from recess 30 for further downstream protocols or assays—such as by scraping or flowing a solution into recess 30. Thus, arcuate or curved bottom wall 50 may facilitate such recovery.

In some embodiments, mat 5 may be used to embed human pluripotent stem cell-derived neuralized embryoid bodies in an extracellular matrix. Once embedded in extracellular matrix, the neuralized embryoid bodies may be dislodged from recess 30 into a culture medium that stimulates the formation of cerebral spheroids, cerebral organoids or cerebral organoid tissue from the neuralized embryoid bodies.

In some embodiments, mat 5 may be used to embed different types of aggregates of cells in an extracellular matrix substantially as described above.

In a different specific application of device 1 of this disclosure, mat 5 may be used to prepare a sample within recess 30 for gel electrophoresis. For example, a sample of nucleic acid or protein may be combined and mixed with other solutions, as applicable, such as a sample buffer, loading dye, diluents, etc., prior to loading the mixture into a well of an agarose or polyacrylamide gel.

Furthermore, the skilled person will readily be able to adapt mat 5 for any other application, not explicitly described herein.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A method for manipulating a biological sample, the method comprising:
   a) providing a resilient and foldable silicone-based mat comprising an anti-static additive, the mat having a top planar surface spaced apart from a bottom planar surface and a plurality of recesses arranged in rows and columns and formed in the top planar surface extending toward the bottom planar surface, the recesses having an opening at the top planar surface and bounded by a non-planar and curved or arcuate bottom wall, wherein a width of each of the plurality of recesses is about 0.5 cm and a depth of each recess measured vertically from a center of the opening at the top planar surface to the bottom wall is about 0.1 cm, and wherein any two adjacent recesses in the column or row direction are separated by the same pitch of between about 0.5 and 1 cm;
   b) enveloping the biological sample in at least one of the recesses within a polymerizable solution; and
   c) recovering the at least one enveloped biological sample from the mat,
   wherein the biological sample is an aggregation of cells, and wherein the aggregation of cells comprises an embryoid body, a spheroid, an organoid, an assembloid, a tissue, or a tissue fragment.

2. The method according to claim 1, further comprising dispensing the solution into the at least one of the recesses.

3. The method according to claim 2, further comprising suspending the biological sample in the solution before dispensing the solution into the at least one of the empty recesses.

4. The method according to claim 2, further comprising positioning the biological sample in the at least one of the recesses before dispensing the solution therein.

5. The method according to claim 1, wherein recovering is by dislodging the at least one enveloped biological sample from the mat.

6. The method according to claim 5, wherein dislodging comprises scraping or flowing a solution into the at least one of the recesses.

7. The method according to claim 5, further comprising bending or folding the mat to dislodge the at least one enveloped biological sample from the mat.

8. The method according to claim 1, wherein the bottom wall is substantially smooth.

9. The method according to claim 1, wherein the mat is homogeneous.

10. The method according to claim 1, wherein the mat is sterilizable.

11. The method according to claim 10, wherein the mat is autoclavable.

12. The method according to claim 1, wherein the mat is dimensioned to fit within a well of a culture vessel.

13. The method according to claim 12, wherein more than one mat fits within the well of the culture vessel.

14. The method according to claim 1, wherein the mat comprises an orientation marker.

15. The method according to claim 1, wherein the aggregation of cells is an embryoid body, a spheroid, an assembloid, a tissue, a tissue fragment, or an organoid.

16. The method according to claim 15, wherein the aggregation of cells comprises pluripotent stem cells or pluripotent stem cell-derived cells.

17. The method according to claim 1, wherein the polymerizable solution comprises at least one extracellular matrix protein.

* * * * *